United States Patent [19]

Singh et al.

[11] Patent Number: 5,916,887
[45] Date of Patent: Jun. 29, 1999

[54] 4-SUBSTITUTED-3-(2-AMINO-2-CYCLOALKYL METHYL)-ACETAMIDO AZETIDIN-2-ONE DERIVATIVES AS CYSTEINE PROTEINASE REGULATORS

[75] Inventors: Rajeshwar Singh; Nian E. Zhou, both of Alberta; Enrico O. Purisima, Montreal; Ronald G. Micetich, Alberta, all of Canada

[73] Assignee: National Research Council of Canada, Ottawa, Canada

[21] Appl. No.: 08/935,259

[22] Filed: Sep. 22, 1997

Related U.S. Application Data

[60] Provisional application No. 60/026,514, Sep. 23, 1996.
[51] Int. Cl.$^6$ .................... A61K 31/395; C07D 205/085; C07D 205/095
[52] U.S. Cl. ......................... 514/210; 540/355; 540/357; 540/359; 540/360
[58] Field of Search ............................ 514/210; 540/355, 540/357, 359, 360

[56] References Cited

FOREIGN PATENT DOCUMENTS 0393457A 10/1990 European Pat. Off. .
WO9632408 10/1996 WIPO .

OTHER PUBLICATIONS

Jewell, Biochemistry 31, 7862–9, 1992.
Thomas, Biochimica et Biophysica Acta 990, 246–253, 1989.
Wang, TiPs 15, p. 412, Nov. 1994.
Otto, Chemical Reviews 97, 133–171, 1997.

*Primary Examiner*—Mark L Berch
*Attorney, Agent, or Firm*—Nikaido Marmelstein Murray & Oram LLP

[57] ABSTRACT

In accordance with the present invention, there are provided 4-substituted-3-(2-amino-2-cycloalkyl methyl)-acetamido azetidin-2-one derivatives of the formula:

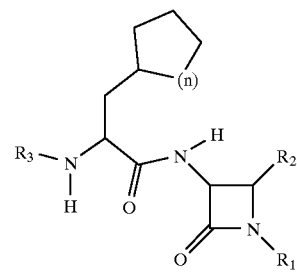

wherein n is 1, 2 or 3; in which $R_1$, $R_2$ and $R_3$ are as defined herein, and salts thereof, which exhibit excellent cysteine proteinase inhibitory activity and which can be used for treatment of different diseases such as muscular dystrophy, myocardial infarction, bone resorption, arthritis, cancer metastasis, pulmonary emphysema, septic shock, cerebral ischemia, memory function, Alzheimer and cataract, malaria, glomerular basement membrane degradation, bacterial infection, inflammatory diseases, parasitic infections, and viral infections.

14 Claims, 1 Drawing Sheet

Figure
In vitro stability of compound 3 and reference compound in rat plasma
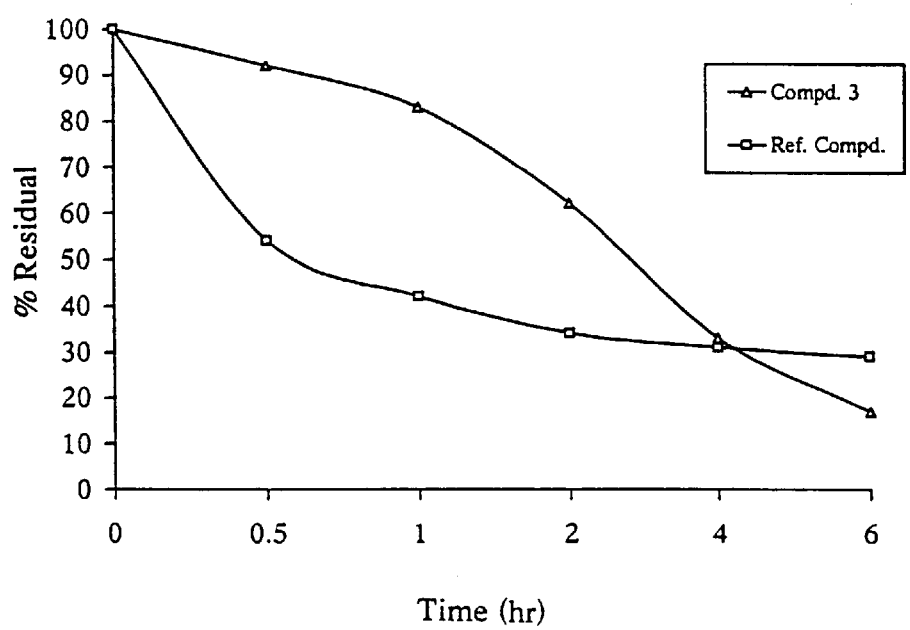

4-SUBSTITUTED-3-(2-AMINO-2-CYCLOALKYL METHYL)-ACETAMIDO AZETIDIN-2-ONE DERIVATIVES AS CYSTEINE PROTEINASE REGULATORS

This application claims priority of U.S. Provisional patent application Ser. No. 60/026,514, filed Sep. 23, 1996.

BACKGROUND OF THE INVENTION

Cysteine proteinases containing a highly reactive cysteine residue with a free thiol group at the active site have been known as playing an important role in certain conditions distinguished by aberrant protein turnover such as: muscular dystrophy (Am. J. Pathol. 1986, 122, 193–198; Am. J. Pathol. 1987, 127, 461–466), myocardial infarction (J. Am. Coll. Cardiol. 1983, 2, 681–688), bone resorption (Biochem. J. 1991, 279, 167–274; J. Biol. Chem. 1996, 271, 2126–2132; and Biochem. Biophys. Acta 1992, 1116, 57–66), arthritis (Arthritis Rheumatism 1994, 37, 236–247; and Biochem. Pharmacol. 1992, 44, 1201–1207), cancer metastasis (Cancer Metastasis Rev. 1990, 9, 333–352), pulmonary emphysema (Am. Rev. Respir. Dis. 1975, 111, 579–586), septic shock (Immunol. Today 1991, 11, 404–410, Biochemistry 1994, 33, 3934–3940), cerebral ischemia, memory function, Alzheimer and cataract (TIPS 1994, 15, 412–419, Bioorg. Med. Chem. Lett. 1995, 4, 387–392, Proc. Natl. Acad. Sci. USA 1991, 88, 10998–11002), malaria (J. Med. Chem. 1995, 38, 5031–5037), glomerular basement membrane degradation (Biochem Bioph. Acta 1989, 990, 246–251), bacterial infection (Nature 1989, 337, 385–386), inflammatory diseases (Protein Science 1995, 4, 3–12), parasitic infections (Annu. Rev. Microbiol. 1993, 47, 821–853; Parasitol. Today 1990, 6, 270–275), and viral infections (Biochem. 1992, 31, 7862–7869).

A variety of cysteine proteinases have been shown to be present in mammalian tissue. The most notable of these proteinases are the lysosomal cathepsins (cathepsin B, H, S, L and K) and the cytoplasmic $Ca^{+2}$ dependent enzymes, the calpains. These enzymes are, therefore, excellent targets for specific inhibitors as therapeutic agents for the conditions such as those noted above.

Cysteine proteinases are inhibited by several types of peptide derived inhibitors such as peptidyl aldehyde (Eur. J. Biochem. 1982, 129, 33–41), chloromethyl ketone (Acta. Biol. Med. Ger. 1981, 40, 1503–1511), diazomethyl ketone (Biochemistry 1977, 16, 5857–5861), monofluoromethyl ketone (Biochemical Pharmacology 1992 44, 1201–1207), acyloxy methyl ketone (J. Med. Chem. 1994, 37, 1833–1840), O-acyl hydroxamates (Biochem. Biophy. Research Communications 1988, 155, 1201–1206), methyl sulphonium salts (J. Biol. Chem. 1988, 263, 2768–2772) and epoxy succinyl derivatives (Agric. Biol. Chem. 1978, 42, 523–527) without significantly inhibiting other classes of proteinases.

SUMMARY OF THE INVENTION

Our laboratory has been extensively involved in search for novel cysteine proteinase regulators and found that 4-substituted-3-(amino-2-cycloalkyl methyl)-acetamido azetidin-2-one derivatives exhibit excellent activity and selectivity within the class of cysteine proteinases. There is an ongoing need to improve in vivo efficacy by improving plasma stability and pharmacokinetics.

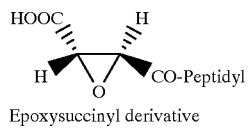

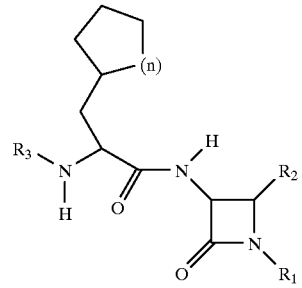

The molecular modelling of 3-substituted phenyl alanyl azetidinone suggested that the replacement of phenyl alanine with cyclohexyl alanine might increase the hydrophobic binding with cysteine proteinases. Unfortunately, there is no increase in activity as expected but it showed improved stability in plasma and good in vivo activity. This finding of novel 4-substituted-3-(2-amino-2-cycloalkyl methyl)-acetamido azetidin-2-one derivatives is reported in the present invention as cysteine proteinase inhibitors.

In accordance with the present invention, there are provided 4-substituted-3-(2-amino-2-cycloalkyl methyl)-acetamido azetidin-2-one derivatives which exhibit cysteine proteinase regulatory (e.g., inhibitory) activity with improved stability in biological fluids and which can be used for treatment of different diseases such as muscular dystrophy, myocardial infarction, bone resorption, arthritis, cancer metastasis, pulmonary emphysema, septic shock, cerebral ischemia, memory function, Alzheimer and cataract, malaria, glomerular basement membrane degradation, bacterial infection, inflammatory diseases, parasitic infections, and viral infections.

In accordance with the present invention, there are provided compounds of formula I and pharmaceutically acceptable salts thereof:

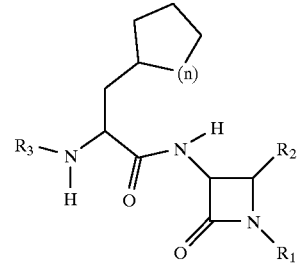

wherein
n is 1, 2 or 3;
$R_1$ is
  hydrogen; or
  $—SO_3^-M^+$ wherein M is a hydrogen atom, a metal ion which is selected from sodium, potassium, magnesium, and calcium, or $N^+(R_4)_4$ wherein $R_4$ is a $C_1$–$C_6$ alkyl group;

$R_2$ is
- (a) a group —$OCOR_5$ wherein $R_5$ is
  - (i) a $C_1$–$C_6$ alkyl group,
  - (ii) a $C_2$–$C_6$ alkenyl group,
  - (iii) a $C_2$–$C_6$ alkynyl group,
  - (iv) a $C_3$–$C_6$ cycloalkyl group,
  - (v) a phenyl group,
  - (vi) a naphthyl group, or
  - (vii) a monocyclic or bicyclic heterocyclic group, which group (i), (ii), (iii), (iv), (v), (vi), or (vii) is unsubstituted or substituted by 1, 2 or 3 substituents independently selected from
    hydroxy,
    halogen,
    carboxy,
    $C_1$–$C_4$ alkyl (which is unsubstituted or substituted at least once with carboxy and/or amino),
    $C_1$–$C_2$ alkoxy,
    amino, and
    cyano, and
    phenyl and monocyclic or bicyclic heterocyclic groups, which phenyl and heterocyclic groups are unsubstituted or substituted by 1 or 2 substituents independently selected from
    hydroxy,
    halogen,
    carboxy,
    $C_1$–$C_4$ alkyl,
    $C_1$–$C_2$ alkoxy,
    amino, and
    cyano;
- or (b) a group —$XR_5$ wherein X is selected from the group consisting of O, S, SO, and $SO_2$, and $R_5$ is as defined above;

$R_3$ is hydrogen, —$COOR_5$, —$COR_5$, —$SO_2R_5$, or —$COR_{14}$ wherein $R_5$ is as defined above and $R_{14}$ is amino group which is unsubstituted or substituted at least once with $C_1$–$C_6$ alkyl group which is unsubstituted or substituted at least once with 1 or 2 substitutents selected from hydroxy, halogen, cyano, amino, heterocycle, and phenyl (wherein the heterocycle or phenyl is unsubstituted or substituted at least once by 1 or 2 substituents selected from halogen, hydroxy, cyano, carboxy and amino).

In accordance with a preferred aspect of the present invention, there are provided compounds of formula I and pharmaceutically acceptable salts thereof:
wherein:
n is 1, 2 or 3
$R_1$ is
  hydrogen;
  —$SO_3^-M^+$ wherein M is a hydrogen atom, a metal ion which is selected from sodium, potassium, magnesium, or calcium, or $N^+(R_4)_4$ wherein $R_4$ is a $C_1$–$C_6$ alkyl group;
$R_2$ is
  —$OCOR_5$ wherein $R_5$ is
  (i) a $C_1$–$C_6$ alkyl group which is unsubstituted or substituted at least once by 1 or 2 substitutents selected from hydroxy, halogen, and amino; or
  (ii) a phenyl group which is unsubstituted or substituted at least once by 1–3 substituents selected from hydroxy, halogen, $C_1$–$C_4$ alkyl group, $C_1$–$C_2$ alkoxy group, and cyano;
  —$XR_6$ wherein X is O, S, SO, or $SO_2$; $R_6$ is
  (i) a $C_1$–$C_6$ alkyl group which is unsubstituted or substituted at least once by 1 or 2 substituents selected from hydroxy, halogen, amino or phenyl; or
  (ii) a phenyl group which is unsubstituted or substituted at least once by 1–3 substituents selected from hydroxy, halogen, carboxy, and $C_1$–$C_4$ alkyl group which is unsubstituted or substituted at least once with carboxy, amino or both, $C_1$–$C_2$ alkoxy group, cyano or heterocycle group;

$R_3$ is
  hydrogen;
  —$COOR_7$ wherein $R_7$ is a $C_1$–$C_6$ alkyl group which is unsubstituted or substituted at least once with phenyl and/or heterocycle group;
  —$COR_8$ wherein $R_8$ is
  (i) a $C_1$–$C_6$ alkyl group which is unsubstituted or substituted at least once by 1 or 2 substitutents selected from hydroxy, halogen, cyano, amino, heterocycle, and phenyl, wherein said heterocycle or phenyl is unsubstituted or substituted at least once by 1 or 2 substituents selected from halogen, hydroxy, cyano, carboxy and amino; or
  (ii) an amino group which is unsubstituted or substituted at least once with $C_1$–$C_6$ alkyl group which is unsubstituted or substituted at least once by 1 or 2 substitutents selected from hydroxy, halogen, cyano, amino, heterocycle and phenyl, wherein said heterocycle or phenyl is unsubstituted or substituted at least once by 1 or 2 substituents selected from halogen, hydroxy, cyano, carboxy and amino; or
  —$SO_2R_9$ wherein $R_9$ is
  (i) a $C_1$–$C_6$ alkyl group which is unsubstituted or substituted at least once with heterocycle and/or phenyl; or
  (ii) a $C_2$–$C_4$ alkenyl group which is unsubstituted or substituted at least once with heterocycle and/or phenyl.

The pharmaceutically acceptable salts of formula I are selected from salts of sodium, potassium, magnesium, calcium, hydrogen chloride, tartaric acid, succinic acid, fumaric acid or p-toluenesulfonic acid.

Examples of $C_1$–$C_6$ alkyl group as substituents in $R_4$, $R_5$, $R_6$, $R_8$, or $R_9$ are straight or branched chain alkyl group having 1–6 carbon atoms such as methyl, ethyl, propyl, 1-methylethyl, butyl, 1-methylpropyl, 2-methylprop-1-yl, 2-methylprop-2-yl, pentyl, 3-methylbutyl, hexyl and the like.

Examples of halogen atoms as substituents in $R_5$, $R_6$, or $R_9$ are fluorine, chlorine, bromine or iodine.

Examples of $C_2$–$C_4$ alkenyl group as defined in $R_9$ are alkenyl group having 2–4 carbon atoms such as ethenyl, 1-propenyl, 2-propenyl, 1-butenyl, 3-butenyl and the like.

Suitable heterocyclic groups in accordance with the present invention include 5- or 6-membered aromatic or non-aromatic heterocyclic groups containing 1, 2, 3 or 4 heteroatoms selected from O, S or N, and bicyclic heterocyclic groups including a monocyclic heterocyclic as defined above which is fused to a second 5- or 6-membered carbocyclic or 5- or 6-membered heterocyclic ring.

Examples of heterocyclic group as defined in $R_5$, $R_6$, $R_7$, $R_8$ or $R_9$ are $C_2$–$C_9$ mono or bicyclic heterocyclic group which may have 1–3 heteroatoms selected from nitrogen, sulphur or oxygen such as thiophene, pyridine, 1,2,3-triazole, 1,2,4-triazole, quinoline, benzofuran, benzothiophene, morpholine, thiomorpholine, piperizine, piperidine and the like.

Examples of $C_1$–$C_4$ alkyl group as substituents in $R_5$, $R_6$, or $R_9$ are methyl, ethyl, propyl, 2-methyl propyl, butyl, 1,1-dimethyl ethyl and the like.

Examples of $C_1$–$C_2$ alkoxy group as substituents in $R_5$, $R_6$, or $R_9$ are methoxy or ethoxy.

The azetidinone nucleus carries two asymmetric carbon atoms at position 3 and 4, and can exist as 4-diastereoisomers. In general, the preferred isomer is that in which the hydrogen atoms at C3 and C4 are cis to each other for superior inhibitory activity against different cysteine proteinase such as papain, Cathepsin B, Cathepsin H, Cathepsin K and Cathepsin L. Such diastereoisomers and their racemic mixtures are also included within use of the azetidinone derivatives as cystein proteinase inhibitor.

In accordance with preferred embodiments of the invention, there are provided 4-substituted-3-(2-amino-2-cycloalkyl methyl)-acetamido azetidin-2-one derivatives of formula I:

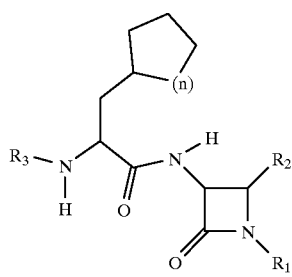

I wherein:

n is 1, 2 or 3

$R_1$ is selected from hydrogen, or sulphonic acid;

$R_2$ is selected from acetoxy, butyloxy, 2-carboxy ethyloxy, 2-aminoethyloxy, 2-fluoro ethoxy, phenoxy, methyl phenoxy, morpholino phenyloxy, 2-hydroxy ethylthio, phenylthio, phenylsulphonyl, 4-(2-carboxy-2-amino ethyl)-phenoxy, 4-carboxy phenoxy, 3-carboxy phenoxy, 2-pyridylthio, 4-pyridylthio, benzyloxy and the like; and $R_3$ is selected from alkanoyl, aryloxy carbonyl, 3-aryl propanoyl, 3-heteroaryl propanoyl, arylmethylaminocarbonyl, 2-aryl-eth-1-en-sulphonyl, and the like.

Preferred embodiments of the present invention include the following compounds:

(3S,4S)-3-(2S-2-benzyloxycarbonylamino-2-cyclohexylmethyl-acetamido)-4-acetoxy-azetidin-2-one;

(3S,4S)-3-{2S-2-(3-phenylpropionoyl)amino-2-cyclohexylmethyl-acetamido}-4-acetoxy-azetidin-2-one;

(3S,4S)-3-{2S-2-(3-phenylpropionoyl)amino-2-cyclohexylmethyl-acetamido}-4-{4-(2S-2-amino-2-carboxy-ethyl)-phenoxy}-azetidin-2-one;

(3S,4R)-3-{2S-2-(3-phenylpropionoyl)amino-2-cyclohexylmethyl-acetamido}-4-{4-(2S-2-amino-2-carboxy-ethyl)-phenoxy}-azetidin-2-one;

(3S,4SR)-3-{2S-2-(3-phenylpropionoyl)amino-2-cyclohexylmethyl-acetamido}-4-phenylthio-azetidin-2-one;

(3S,4SR)-3-{2S-2-(3-phenylpropionoyl)amino-2-cyclohexylmethyl-acetamido}-4-phenylsulfonyl-azetidin-2-one;

(3S,4S)-3-{2S-2-(benzylaminocarbonyl)amino-2-cyclohexylmethyl-acetamido}-4-acetoxy-azetidin-2-one;

(3S,4S)-3-{2S-2-(phenylethenylsulfonyl)amino-2-cyclohexylmethyl-acetamido}-4-acetoxy-azetidin-2-one;

(3S,4S)-3-(2S-2-benzyloxycarbonylamino-2-cyclohexylmethyl-acetamido)-4-(3-methyl-phenoxy)-azetidin-2-one;

(3S,4R)-3-(2S-2-benzyloxycarbonylamino-2-cyclohexylmethyl-acetamido)-4-(3-methyl-phenoxy)-azetidin-2-one;

(3S,4S)-3-{2S-2-[3-(pyridin-4-yl)propenoyl]amino-2-cyclohexylmethyl-acetamido}-4-phenoxy-azetidin-2-one; and (3S,4S)-3-{2S-2-[3-(pyridin-3-yl)propenoyl]amino-2-cyclohexylmethyl-acetamido}-4-phenoxy-azetidin-2-one.

Compounds of formula I may be utilized for different diseases such as muscular dystrophy, myocardial infarction, bone resorption, arthritis, cancer metastasis, pulmonary emphysema, septic shock, cerebral ischemia, memory function, Alzheimer and cataract, malaria, glomerular basement membrane degradation, bacterial infection, inflammatory diseases, parasitic infections, and viral infections by regulating the cysteine proteinases in medicaments formulated with pharmaceutically acceptable carriers.

BRIEF DESCRIPTION OF THE DRAWING FIGURE

The FIGURE is a graph of in vitro stability of compound 3 (see Example 3) and a reference compound in rat plasma.

DESCRIPTION OF PREFERRED EMBODIMENTS

The present invention relates to certain 3,4-disubstituted-azetidin-2-one derivatives having cysteine proteinase inhibitory activity and stability in biological fluids. The compounds of this invention include compounds having hydrogen, ester ($OCOR_5$), ether ($OR_5$), thioether ($SR_5$), sulfone ($SO2R_5$) and sulfoxide ($SOR_5$) at position 4 and cycloalkyl alanine group at position 3 of 3-amino-azetidin-2-one (II). Certain derivatives of formula I are prepared by the common intermediates II by reacting with cycloalkyl alanine either in presence of dicyclohexylcarbidiimide (DCC) or acid chloride in presence of base, or activated ester according to techniques known in the art.

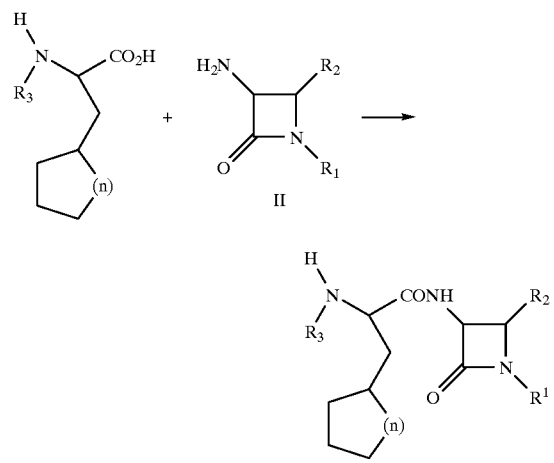

The preparation of compounds II is carried out by following the synthetic route as described in Eur. J. Med. Chem 1992, 27, 131–140, and Tetrahedron 1983, 39, 2577–2589, wherein $R_2$ is $OCOR_5$, and $R_3$ is a substituent group $COOR_7$. The definitions of $R_1$, $R_5$ and $R_7$ are the same as defined above.

Certain 4-substituted-3-(2-amino-2-cycloalkyl methyl)-acetamido azetidin-2-one derivatives of formula I wherein substititions at the amino acid group are other than $COOR_5$, such as $COR_5$ or $SO_2R_5$ are prepared by following the synthetic route as shown in the scheme depicted below. The $R_5$ groups are the same as defined above.

$R_2$ is $OCOCH_3$ by reacting with $R_5XH$ in presence of Lewis acids such as zinc acetate, zinc iodide, zinc chloride, titanium tetrachloride, palladium acetate, boron trifluoride, aluminum trichloride and the like or in presence of base such

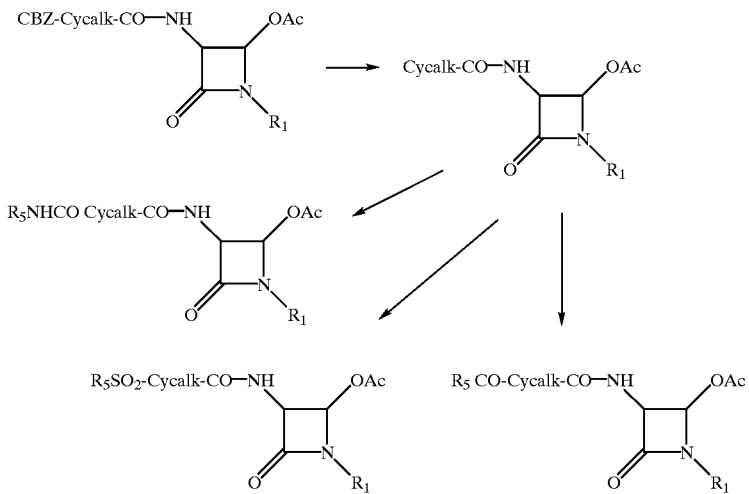

The benzyloxycarbonyl cyclohexyl alanine are desubstituted and resubstituted through amide bond by reacting with $R_5$—COOH either in presence of DCC or acid chloride in presence of base or anhydride in presence of base or activated ester, or through sulphonamide bond by reacting with $R_5SO_2Cl$ in presence of base or through urea bond by reacting with $R_5NCO$. $R_{11}$ is a $C_1$–$C_6$ alkyl group which is unsubstituted or substituted with phenyl or heterocyclic group.

as sodium hydroxide. There are cases where carboxy group as substituent in $R_5$ is substituted with $R_{11}$ such as diphenyl methyl or 1,1-dimethyl ethyl, or amino group as substituent in $R_5$ is substituted with $R_{12}$ such as benzyloxy carbonyl or 1,1-dimethyl ethoxy carbonyl, or both groups as substituents in $R_5$ together are desubstituted by hydrogenation or hydrolysis with acids.

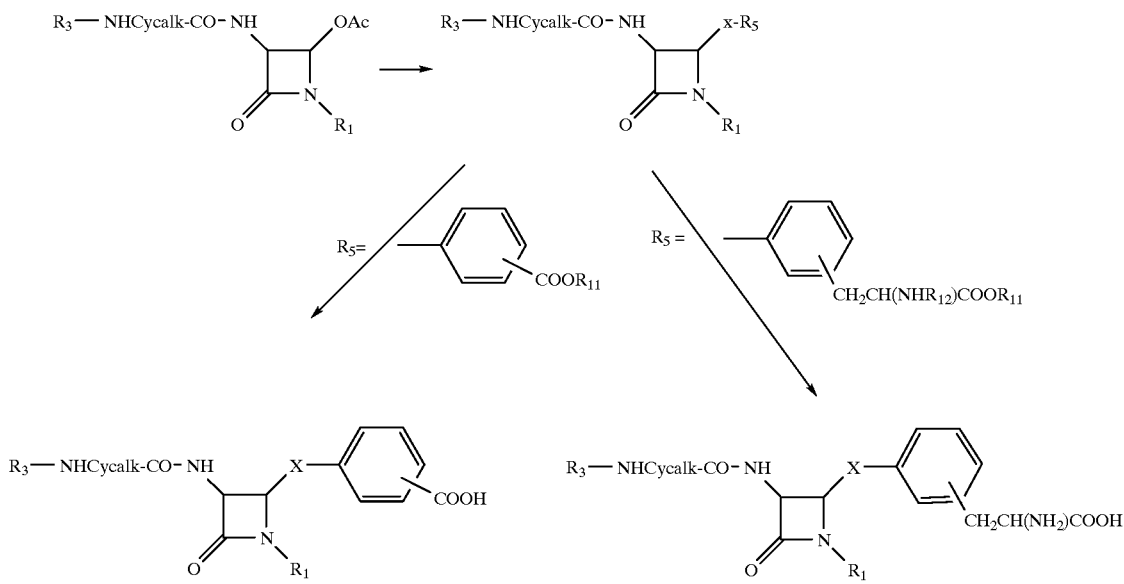

Certain 4-substituted-3-(2-amino-2-cycloalkyl methyl)-acetamido azetidin-2-one derivatives of formula I wherein $R_2$ is $XR_5$, wherein X is O or S, and $R_5$ is the same as defined above, are prepared by following the synthetic route as shown below starting from compound of formula I wherein Certain 4-substituted-3-(2-amino-2-cyclo-alkyl methyl)-acetamido azetidin-2-one derivatives of formula I wherein $R_2$ is $SR_5$ are converted to $SOR_5$ or $SO_2R_5$ by oxidation with oxidizing agent selected from m-chloroperbenzoic acid, hydrogen peroxide, peracetic acid, potassium permanganate, magnesium dioxide and the like. The synthetic route is outlined below.

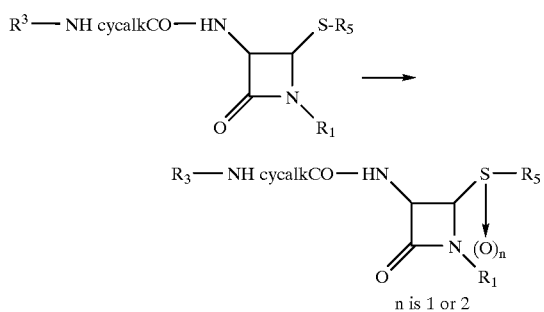

4-substituted-3-(2-amino-2-cycloalkyl methyl)-acetamido azetidin-2-one derivatives of formula I wherein $R_1$ is hydrogen can be converted to N-sulphonic acid by the sulphonation with pyridine-$SO_3$ or dimethylformamide-$SO_3$ complex by following the synthetic route as outlined below.

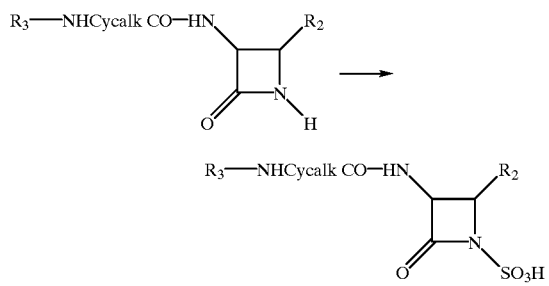

In the above descriptions, the reactants are reacted together with solvent at elevated or low temperatures for sufficient time to allow the reaction to proceed to completion. The reaction conditions will depend upon the nature and reactivity of the reactants. Wherever a base is used in a reaction, they are selected from triethylamine, pyridine, 4-dimethylaminopyridine, diisopropylethylamine, 1,5-diazabicyclo[4,3,0]non-5-ene, 1,8-diazabicyclo[5,4,0]undec-7-ene, sodium carbonate, potassium carbonate or cesium carbonate.

The solvent of choice for the reaction is selected from non-reactive solvents depending on the reactants such as benzene, toluene, acetonitrile, tetrahydrofuran, ethanol, methanol, chloroform, ethyl acetate, methylene chloride, dimethyl formamide, dimethyl sulphoxide, hexamethyl phosphoric triamide, or the like. Solvent mixtures may also be utilized.

Suitable reaction temperatures are generally in the range of from −70° C. to 150° C. The preferred molar ratio of reactants is 1:1 to 1:5. The reaction time is in the range of from 0.5 to 72 hours, depending on the reactants.

The desubstitution of N-substituent group is carried out either by hydrogenation or by hydrolysis with appropriate acids such as hydrochloric acid, trifluoroacetic acid or acetic acid in solvent such as methanol, ethanol, propanol or ethyl acetate. The hydrogenation reaction is usually carried out in the presence of a metal catalyst, such as Pd, Pt, or Rh, under normal pressure to high pressure.

The compounds of this invention, when used alone or in combination with other drugs as an agent for treating muscular dystrophy, osteoporosis or cancer metastasis in mammals including humans, may take pharmaceutical dosage forms including parenteral preparations such as injections, suppositories, aerosols and the like, and oral preparations such as tablets, coated tablets, powders, granules, capsules, liquids and the like. Injections are generally preferred. The above preparations are formulated in a manner known in the art.

For the formulation of solid preparations for oral administration, an excipient, and if desired, a binder, disintegrator, lubricant, coloring agent, corrigent, flavor etc. are added to the compound of the invention, and then tablets, coated tablets, granules, powders, capsules or the like are prepared in a conventional manner.

For the formulation of injections, a pH adjusting agent, buffer, stabilizer, isotonic agent, local anesthetic or the like is added to the active ingredient of the invention, and injections for subcutaneous, intramuscular or intravenous administration can be prepared in the conventional manner.

For the formulation of suppositories, a base, and if desired, a surfactant are added to the active ingredient of the invention, and the suppositories are prepared in a conventional manner.

The excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, schellac, sucrose, water, ethanol, propanol, carboxymethyl cellulose, potassium phosphate and the like, lubricants such as magnesium stearate, talc and the like, and further include additives such as usual known colouring agents, disintegrators and the like. Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives.

The amount of the compound I of the invention to be incorporated into the pharmaceutical composition of the invention varies with the dosage form, solubility and chemical properties of the compound, administration route, administration scheme and the like. Preferably, the amount is about 1 to 25% (w/w) in the case of oral preparations, and about 0.1 to about 5% (w/w) in the case of injections which are parenteral preparations.

The dosage of the compound I of the invention is suitably determined depending on the individual cases taking symptoms, age and sex of the subject and the like into consideration. Usually the dosage in the case of oral administration is about 50 to 1500 mg per day for an adult in 2 to 4 divided doses, and the dosage in the case of injection, for example, by intravenous administration is 2 ml (about 1 to 100 mg) which is administered once a day for adults wherein the injection may be diluted with physiological saline or glucose injection liquid if so desired, and slowly administered over at least 5 minutes. The dosage in case of suppositories is about 1 to 1000 mg which is administered once or twice a day at an interval of 6 to 12 hours wherein the suppositories are administered by insertion into the rectum.

EXAMPLE 1

(3S,4S)-3-(2S-2-benzyloxycarbonylamino-2-cyclohexylmethyl-acetamido)-4-acetoxy-azetidin-2-one (1)

(3S,4S)-3-benzyloxycarbonylamino-4-acetoxy-azetidin-2-one (912 mg, 3.28 mmol) is hydrogenated with 1 g of 10% palladium on activated carbon in 35 ml of ethyl acetate at 50 psi hydrogen pressure at room temperature for 1.5 hours. After removal of catalyst by filtration, desubstitution (3S, 4S)-3-amino-4-acetoxy-azetidin-2-one in ethyl acetate is obtained.

To a solution of 2S-2-benzyloxycarbonylamino-2-cyclohexylmethyl-acetic acid (1.0 g, 3.28 mmol) and 1-hydroxy-benzotriazole (443 mg, 3.28 mmol) in THF (30 ml), DCC (676 mg, 3.28 mmol)/THF (10 ml) is added at 0° C. The reaction mixture is stirred at room temperature for 2 hours and then cooled with an ice bath. The resulting DCU is removed by filtration. Then, a precooled solution of (3S,4S)-3-amino-4-acetoxy-azetidin-2-one in ethyl acetate is added at −15° C. and the resulting mixture is stirred at a bath temperature of −15 to 5° C. for 1 hour and then at room temperature for 3 hours. After removal of solvent, the residue is dissolved in ethyl acetate, washed with cold saturated $NaHCO_3$ solution, water, brine and dried over sodium sulphate. After removal of solvent, the residue is purified by silica gel column chromatography using hexane-ethyl acetate (1:1) as eluent and the title compound is obtained.

Yield: 92%, m.p.: 134–135° C., FAB-MS: 432 (MH$^+$), calcd for $C_{22}H_{29}N_3O_6$ 431

$^1$H NMR (DMSO-d$_6$), δ (ppm): 0.75–1.8 (13 H, m), 2.08 (3H, s), 4.00–4.15 (1H, m), 4.64 (1H, d, J=8 Hz), 5.04 (2H, m), 5.75 (1H, s), 7.30–7.45 (5H, m), 7.48 (1H, d, J=8 Hz), 8.67 (1H, d, J=8.3 Hz), 9.16 (1H, s).

IR (KBr, cm$^{-1}$): 3325, 2925, 1797, 1747, 1693, 1661, 1536, 1446, 1371, 1270, 1227.

EXAMPLE 2

(3S,4S)-3-{2S-2-(3-phenylpropionoyl)amino-2-cyclohexylmethyl-acetamido}-4-acetoxy-azetidin-2-one (2)

By a similar method as described in example 1, the title compound is obtained by reacting 2S-2-(3-phenylpropionoyl)amino-2-cyclohexylmethyl-acetic acid with (3S,4S)-3-amino-4-acetoxy-azetidin-2-one.

Yield: 85%, m.p.: 166–168° C. (dec.), FAB-MS: 430 (MH$^+$), calcd for $C_{23}H_{31}N_3O_5$ 429

$^1$H NMR (CDCl$_3$-d$_6$), δ (ppm): 0.80–1.80 (13H, m), 2.10 (3H, s), 2.53 (2H, t, J=7.5 Hz), 2.94 (2H, t, J=7.5 Hz), 4.54 (1H, m), 4.62 (1H, d, J=7.5 Hz), 5.80 (1H, s), 6.18 (1H, d, J=8.1 Hz), 7.10–7.35 (6H, m), 7.54 (1H, d, J=7.5 Hz).

IR (KBr, cm$^{-1}$): 3275, 2925, 1794, 1739, 1656, 1634, 1531, 1440, 1358, 1219.

EXAMPLE 3

(3S,4S)-3-{2S-2-(3-phenylpropionoyl)amino-2-cyclohexylmethyl-acetamido}-4-{4-(2S-2-amino-2-carboxy-ethyl)-phenoxy}-azetidin-2-one (3)

A mixture of (3S,4S)-3-{2S-2-(3-phenylpropionoyl) amino-2-cyclohexylmethyl-acetamido}-4-acetoxy-azetidin-2-one (550 mg, 1.28 mmol), 4-(2S-2-N-benzyloxycarbonylamino-2-diphenylmethoxycarbonyl-ethyl)-phenol (481 mg, 1 mmol), and zinc acetate dihydrate (300 mg, 1.36 mmol) in a mixture of benzene (18 ml) and toluene (18 ml) is refluxed for 5 hours using Dean-Stark water separator. The reaction mixture is purified by silica gel column chromatography using hexane-ethyl acetate as eluent and 200 mg of (3S,4S)-3-{2S-2-(3-phenylpropionoyl) amino-2-cyclohexylmethyl-acetamido}-4-{(2S-2-N-benzyloxy-carbonylamino-2-diphenylmethoxycarbonyl-ethyl)-phenoxy}-azetidin-2-one is obtained.

$^1$H NMR (CDCl$_3$-d$_6$), δ (ppm): 0.80–1.80 (13H, m), 2.45 (2H, t, J=7.5 Hz), 2.87 (2H, t, J=7.5 Hz), 3.01 (2H, m), 4.45–4.70 (3H, m), 5.03 (2H, s), 5.60 (1H, s), 6.50–6.90 (6H, m), 7.1–7.4 (21H, m), 7.58 (1H, d, J=7.5 Hz).

200 mg of (3S,4S)-3-{2S-2-(3-phenylpropionoyl)amino-2-cyclohexylmethyl-acetamido}-4-{(2S-2-N-benzyloxy-carbonyl amino-2-diphenylmethoxycarbonyl-ethyl)-phenoxy}-azetidin-2-one is hydrogenated with 500 mg of 10% palladium on activated carbon in 50 ml of ethyl acetate at 50 psi hydrogen pressure at room temperature for 2.5 hours. The solid is filtered and washed with ethyl acetate (3×10 ml). The solid is extracted with a mixture of water/acetonitrile (3:7) (3×20 ml). After removal of solvent, 31 mg of the title compound is obtained as white solid.

Yield: 24%, m.p.: 180° C. (dec.), FAB-MS: 551 (MH$^+$), calcd for $C_{30}H_{38}N_4O_6$ 550

$^1$H NMR (DMSO-d$_6$), δ (ppm): 0.7–1.8 (13H, m), 2.35–2.55 (2H, m), 2.70–2.90 (2H, m), 3.20–3.40 (2H, m), 4.29 (1H, m), 4.65 (1H, d, J=8 Hz), 5.49 (1H, s), 6.83 (2H, m), 7.15–7.35 (7H, m), 8.10 (1H, d, J=8 Hz), 8.75 (1H, d, J=8 Hz), 9.32 (1H, s).

IR (KBr, cm$^{-1}$): 3385, 2925, 1791, 1750, 1681, 1647, 1623, 1556, 1522, 1384, 1227.

EXAMPLE 4

(3S,4R)-3-{2S-2-(3-phenylpropionoyl)amino-2-cyclohexylmethyl-acetamido}-4-{4-(2S-2-amino-2-carboxy-ethyl)-phenoxy}-azetidin-2-one (4)

To a solution of 4-(2S-2-N-benzyloxycarbonylamino-2-diphenylmethoxy carbonyl-ethyl)-phenol (7.46 g, 15.6 mmol) in acetone (80 ml), H$_2$O (20 ml) and 1 N NaOH (14 ml), (3S,4S)-3-{2S-2-(3-phenylpropionoyl)amino-2-cyclohexylmethyl-acetamido}-4-acetoxy-azetidin-2-one (5.51 g, 12.8 mmol) in acetone (100 ml) and H$_2$O (50 ml) is slowly added at 5° C. The mixture is stirred at 5° C. for 2 hours. After removal of solvent, the residue is dissolved in ethyl acetate, washed with water, brine and dried over sodium sulphate. After removal of solvent, the residue is recrystallized from methanol/ethyl acetate/hexane and 2.1 g of (3S,4R)-3-{2S-2-(3-phenylpropionoyl)amino-2-cyclohexylmethyl-acetamido}-4-{(2S-2-N-benzyloxycarbonylamino-2-diphenylmethoxy carbonyl-ethyl)-phenoxy}-azetidin-2-one is obtained as white solid.

910 mg of (3S,4R)-3-{2S-2-(3-phenylpropionoyl)amino-2-cyclohexylmethyl-acetamido}-4-{(2S-2-N-benzyloxycarbonylamino-2-diphenylmethoxycarbonyl-ethyl)-phenoxy}-azetidin-2-one is hydrogenated with 2 g of 10% palladium on activated carbon in a mixture of ethyl acetate (50 ml), THF (50 ml) and ethanol (20 ml) at 50 psi hydrogen pressure at room temperature for 4 hours. The solid is filtered and washed with ethyl acetate (3×20 ml). The solid is extracted with a mixture of water/acetonitrile (4:6) (2×50 ml). After removal of solvent, the resulting solid is washed with acetonitril and 265 mg of the title compound is obtained as white solid.

Yield: 45%, m.p.: 161–162° C., FAB-MS: 551 (MH$^+$), calcd for $C_{30}H_{38}N_4O_6$ 550

$^1$H NMR (DMSO-d$_6$), δ (ppm): 0.7–1.8 (13H, m), 2.35–2.50 (2H, m), 2.7–2.9 (2H, m), 3.2–3.4 (2H, m), 4.35 (1H, m), 5.27 (1H, dd, J=8, 3 Hz), 5.65 (1H, d, J=3 Hz), 6.82 (2H, m), 7.05–7.30 (7H, m), 7.94 (1H, d, J=8 Hz), 8.64 (1H, d, J=8 Hz), 9.28 (1H, s).

IR (KBr, cm$^{-1}$): 3400, 3290, 2925, 1771, 1643, 1555, 1506, 1396, 1230.

EXAMPLE 5

(3S,4SR)-3-{2S-2-(3-phenylpropionoyl)amino-2-cyclohexylmethyl-acetamido}-4-phenylthio-azetidin-2-one (5)

To a solution of thiophenol (149 mg, 1.36 mmol) in THF (5 ml), water (5 ml) and 1 N NaOH (1.2 ml), (3S,4S)-3-{2S-2-(3-phenylpropionoyl)amino-2-cyclohexylmethyl-acetamido}-4-acetoxy-azetidin-2-one (387 mg, 0.9 mmol) in acetone (10 ml) and THF (5 ml) is added at 5° C. The mixture is stirred at 5° C. for 1 hour and then at room temperature for 1 hour. After removal of solvent, the residue is dissolved in ethyl acetate, washed with water, brine and dried over sodium sulphate. After removal of solvent, the residue is purified by recrystallization from THF-ethyl acetate-hexane and 164 mg of title compound is obtained.

Yield: 38%, m.p.: 198–200° C., FAB-MS: 480 (MH$^+$), calcd for C$_{27}$H$_{33}$N$_3$O$_3$S 479

$^1$H NMR (DMSO-d$_6$), δ (ppm): 0.7–17 (13H, m), 2.45 (2H, m), 2.80 (2H, m), 4.34 (0.85H, m), 4.45 (0.15H, m), 4.54 (0.85H, dd, J=8.5, 2.0 Hz), 4.92 (0.85H, d, J=2.0 Hz), 5.25–5.35 (0.3H, m), 7.10–7.50 (10H, m), 7.98 (0.15H, d, J=8.1 Hz), 8.05 (0.85H, d, J=8.1 Hz), 8.71 (0.85H, d, J=8.6 Hz), 8.83 (0.15H, d, J=8.6 Hz), 9.00 (1H, s).

IR (KBr, cm$^{-1}$): 3270, 2905, 1763, 1735, 1634, 1523, 1436, 1367, 1222.

EXAMPLE 6

(3S,4SR)-3-{2S-2-(3-phenylpropionoyl)amino-2-cyclohexylmethyl-acetamido}-4-phenylsulfonyl-azetidin-2-one (6)

A mixture of (3S,4SR)-3-{2S-2-(3-phenylpropionoyl)amino-2-cyclohexylmethyl-acetamido}-4-phenylthio-azetidin-2-one (100 mg, 0.208 mmol) obtained in example 5, and KMnO$_4$ (50 mg, 0.32 mmol) in acetic acid (10 ml) and H$_2$O (2 ml) is stirred at 5° C. for 1 hour and then room temperature for 1 hour. One drop of H$_2$O$_2$ (30% aq) is added. The reaction mixture is partitioned between ethyl acetate and water, the organic layer is washed with water, saturated NaHCO$_3$, water, brine and dried over Na$_2$SO$_4$. After removal of the solvent, solid is washed with ether and 78 mg of the title compound is obtained. Yield: 73%, m.p.: 170° C. (dec.), FAB-MS: 512 (MH$^+$), calcd for C$_{27}$H$_{33}$N$_3$O$_5$S 511

$^1$H NMR (DMSO-d$_6$), δ (ppm): 0.6–1.7 (13H, m), 2.45 (2H, m), 2.80 (2H, m), 4.30 (0.85H, m), 4.50 (0.15H, m), 4.87 (0.85H, dd, J=8.2 & 2.1 Hz), 4.95 (0.85H, d, J=2.1 Hz), 5.20 (0.15H, d, J=4.6 Hz), 5.51 (0.15H, m), 7.22 (5H, m), 7.60–8.00 (5H, m), 8.05 (1H, d, J=8.3 Hz), 8.48 (0.15H, d, J=8.4 Hz), 8.71 (0.85H, d, J=8.4 Hz), 9.31 (0.85H, s), 9.40 (0.15H, s).

IR (KBr, cm$^{-1}$): 3280, 2905, 1779, 1640, 1517, 1440, 1301.

EXAMPLE 7

(3S,4S)-3-{2S-2-(benzylaminocarbonyl)amino-2-cyclohexylmethyl-acetamido}-4-acetoxy-azetidin-2-one (7)

(3S,4S)-3-{2S-2-(benzyloxycarbonyl)amino-2-cyclohexylmethyl-acetamido}-4-acetoxy-azetidin-2-one (from example 1) (216 mg, 0.5 mmol) is hydrogenated with 400 mg of 10% palladium on activated carbon in ethyl acetate (15 ml) and THF (7 ml) at 50 psi hydrogen pressure at room temperature for 3 hours. After removal of catalyst by filtration, desubstituted (3S,4S)-3-(2S-2-amino-2-cyclohexylmethyl-acetamido}-4-acetoxy-azetidin-2-one in ethyl acetate/THF is cooled to −15° C. and then benzyl isocyanate (106 mg, 0.8 mmol) is added. The reaction mixture is stirred at −10 to 0° C. for 1 hour and room temperature for 1 hour. After removal of solvent, the residue is dissolved in ethyl acetate, washed with cold saturated NaHCO$_3$ solution, water, brine and dried over sodium sulphate. After removal of solvent, the residue is purified by silica gel column chromatography using hexane-ethyl acetate (1:2) as eluent and the title compound is obtained.

Yield: 74%, m.p.: 192–194° C., FAB-MS: 431 (MH$^+$), calcd for C$_{22}$H$_{30}$N$_4$O$_5$ 430

$^1$H NMR (DMSO-d$_6$), δ (ppm): 0.7–1.8 (13H, m), 2.07 (3H, s), 4.15–4.30 (3H, m), 4.64 (1H, d, J=8.5 Hz), 5.74 (1H, s), 6.15 (1H, d, J=8.6 Hz), 6.46 (1H, m), 4.20–4.35 (5H, m), 8.71 (1H, d, J=8.5 Hz), 9.16 (1H, s).

IR (KBr, cm$^{-1}$): 3325, 2905, 1789, 1732, 1653, 1628, 1554, 1526, 1440, 1357, 1223.

EXAMPLE 8

(3S,4S)-3-{2S-2-(phenylethenylsulfonyl)amino-2-cyclohexylmethyl-acetamido}-4-acetoxy-azetidin-2-one (8)

(3S,4S)-3-{2S-2-(benzyloxycarbonyl)amino-2-cyclohexylmethyl-acetamido}-4-acetoxy-azetidin-2-one (from example 1) (216 mg, 0.5 mmol) is hydrogenated with 400 mg of 10% palladium on activated carbon in ethyl acetate (15 ml) and THF (7 ml) at 50 psi hydrogen pressure at room temperature for 3 hours. After removal of catalyst by filtration, desubstituted (3S,4S)-3-(2S-2-amino-2-cyclohexylmethyl-acetamido}-4-acetoxy-azetidin-2-one in ethyl acetate/THF is cooled to −15° C. and then triethylamine (50 mg, 0.5 mmol) and benzyl isocyanate (106 mg, 0.8 mmol) is added. The reaction mixture is stirred at −10 to 0° C. for 1 hour and at 5° C. overnight. After removal of solvent, the residue is dissolved in ethyl acetate, washed with cold saturated NaHCO$_3$ solution, water, brine and dried over sodium sulphate. After removal of solvent, the residue is purified by silica gel column chromatography using hexane-ethyl acetate (1:1) as eluent and the title compound is obtained.

Yield: 35%, m.p.: 77° C. (dec.), FAB-MS: 464 (MH$^+$), calcd for C$_{22}$H$_{29}$N$_3$O$_6$S 463

$^1$H NMR (DMSO-d$_6$), δ (ppm): 0.7–1.8 (13H, m), 2.02 (3H, s), 3.70–3.85 (1H, m), 4.61 (1H, d, J=7.6 Hz), 5.54 (1H, s), 6.99 (1H, d, J=15.5 Hz), 7.32 (1H, d, J=15.5 Hz), 7.40–7.50 (3H, m), 7.60–7.70 (2H, m), 7.82 (1H, d, J=7.6 Hz), 8.80 (1H, d, J=8.0 Hz), 9.18 (1H, s).

IR (KBr, cm$^{-1}$): 3295, 2905, 1778, 1744, 1659, 1521, 1441, 1317, 1222.

EXAMPLE 9

(3S,4S)-3-(2S-2-benzyloxycarbonylamino-2-cyclohexylmethyl-acetamido)-4-(3-methyl-phenoxy)-azetidin-2-one (9A) and (3S,4R)-3-(2S-2-benzyloxycarbonyl amino-2-cyclohexylmethyl-acetamido)-4-(3-methyl-phenoxy)-azetidin-2-one (9B)

To a solution of 3-methyl-phenol (81 mg, 0.75 mmole) in acetone (2 ml) and 1N NaOH (0.6 ml, 0.6 mmole), (3S,4S)-

3-(2S-2-benzyloxycarbonylamino-2-cyclohexylmethyl-acetamido)-4-acetoxy-azetidin-2-one (216 mg, 0.5 mmole) in THF (4 ml) and H$_2$O (1 ml) is added at 0° C. The mixture is stirred at 0° C. for 1 hour and then at room temperature for 30 min. After removal of solvent, the residue is dissolved in ethyl acetate, washed with water, brine and dried over sodium sulfate. After removal of solvent, the residue is purified by silica gel column chromatography using hexane-ethyl acetate as eluent. 110 mg of (3S4S)-3-(2S-2-benzyloxycarbonylamino-2-cyclohexyl-methyl-acetamido)-4-(3-methyl-phenoxy)-azetidin-2-one (9A) and 40 mg of (3S,4R)-3-(2S-2-benzyloxycarbonylamino-2-cyclohexylmethyl-acetamido)-4-(3-methyl-phenoxy)-azetidin-2-one (9B) are obtained.

For (9A)
 Yield: 46%
 m.p.: 184–185.5° C.
 $^1$H-NMR (DMSO-d$_6$), δ (ppm): 0.7–1.8 (13H, m), 2.26 (3H,s), 4.0–4.2 (1H, m), 4.64 (1H, d, J=8.5 Hz), 5.05 (2H, m), 5.50 (1H,s), 6.6–6.7 (2H, m), 6.83 (1H,d, J=7.3 Hz), 7.1–7.4 (6H,m), 7.52 (1H,d, J=8 Hz), 8.82 (1H,d, J=8.5 Hz), 9.28 (1H, s).

For (9B)
 Yield: 17%
 m.p.: 178–179° C.
 $^1$H-NMR (DMSO-d$_6$) δ (ppm): 0.7–1.8 (13H, m), 2.24 (3H,s), 4.0–4.2 (1H, m), 5.01 (2H, m), 5.33 (1H,m), 5.68 (1H,d, J=3.7 Hz), 6.6–6.85 (3H,m), 7.1–7.4 (7H, m), 8.61 (1H,d, J=9.2 Hz), 9.23 (1H, s).

EXAMPLE 10

(3S,4S)-3-{2S-2-[3-(pyridin-4-yl)propenoyl]amino-2-cyclohexylmethyl-acetamido}-4-phenoxy-azetidin-2-one (10)

The title compound was synthesized by the reaction of succinimidyl 3-(pyridin-4-yl) propanoic acid with (3S,4S)-3-(2S-2-amino-2-cyclohexylmethyl-acetamido)-4-phenoxy-azetidin-2-one in DMF.

Yield: 43% m.p.: 145–147° C.

$^1$H-NMR (DMSO-d$_6$), δ (ppm): 0.7–1.8 (13H, m), 4.35–3.50 (1H, m), 4.66 (1H, d, J=8.3 Hz), 5.55 (1H,s), 6.86–7.55 (9H, m), 8.54 (1H,d, J=8.0 Hz), 8.60 and 8.65 (2H,2s), 8.93 (1H,d, J=8.4 Hz), 9.31 (1H, s).

EXAMPLE 11

(3S,4S)-3-{2S-2-[3-(pyridin-3-yl)propenoyl]amino-2-cyclohexylmethyl-acetamido}-4-phenoxy-azetidin-2-one (11)

The title compound was synthesized by the reaction of succinimidyl 3-(pyridin-3-yl) propenoic acid with (3S,4S)-3-(2S-2-amino-2-cyclohexylmethyl-acetamido)-4-phenoxy-azetidin-2-one in DMF.

Yield: 47% m.p.: 148–150° C.

$^1$H-NMR (DMSO-d$_6$), δ (ppm): 0.3–1.8(13H,m), 4.42–4.54 (1H, m), 4.67 (1H, d, J=8.0 Hz), 5.55 (1H,s), 6.82–7.56 (8H, m), 7.99 (1H,d, J=7.9 Hz), 8.45 (1H,d, J=8.0 Hz), 8.56 (1H,d, J=4.7 Hz), 8.77 (1H,s), 8.92 (1H, d, J=8.5 Hz), 9.31 (1H, s).

Testing of inhibitors for inhibition of Cathepsin B and L

TEST EXAMPLE 1

In vitro assay procedure for cathepsin B

The compounds of formula I are tested for inhibition of cathepsin B using the known method (A. J. Barret et al., Biochem. J. 1982, 201, 189–198). To 170 μl of an enzyme-buffer mixture (enzyme: recombinant rat cathepsin B, diluted to give approximate 10 Fluorescence units/min, buffer: 56 mM sodium acetate, 1.124 mM EDTA, 10 mM DTT, pH 5.1) 10 μL of inhibitor (dissolved in DMSO) is added. After 10 min of incubation at room temperature, a 20 μl of 5 mM substrate (N-CBZ-Phe-Arg-AMC, dissolved in DMSO) is added to initiate reaction. Reading is followed up for 10 min on a Fluoroskan fluorescence reader (excitation at 380 nm, emission at 460 nm).

A plot of percentage of inhibition vs inhibitor concentration is obtained, and IC$_{50}$ is determined using a linear regression calculation (concentration of inhibitor which will give 50% inhibition).

TEST EXAMPLE 2

In vitro assay procedure for cathepsin L

To 170 μl of enzyme-buffer mixture (enzyme: recombinant rat cathepsin L, diluted to give approximate 15 Fluorescence units/min, buffer: 58.8 mM sodium citrate, 1.18 mM EDTA, 235 mM sodium chloride, 5 mM DTT, pH 5.0) 10 μL of inhibitor (dissolved in DMSO) is added. After 10 min of incubation at room temperature, 20 μl of 1 mM substrate (N-CBZ-Phe-Arg-AMC, dissolved in DMSO) is added to initiate reaction. Reading is followed up for 10 min on a Fluoroskan fluorescence reader (excitation at 380 nm emission at 460 nm).

A plot of percentage of inhibition vs inhibitor concentration is obtained, and IC$_{50}$ is determined using a linear regression calculation (concentration of inhibitor which will give 50% inhibition).

TABLE 1

In vitro inhibitory activity of monobactam compounds on cysteine proteases.

| Example No. | IC$_{50}$ (μM) | |
| --- | --- | --- |
|  | Cathepsin B | Cathepsin L |
| 1 | 8.71 | 0.78 |
| 2 | 11.6 | 2.32 |
| 3 | 34 | 1.82 |
| 4 | 9.2 | 1.8 |
| 5 | 10.4 | 0.016 |
| 6 | 29 | 0.078 |
| 7 | 11.6 | 2.30 |
| 8 | 11 | 2.16 |
| 9A | 6.9 | 0.083 |
| 9B | 0.25 | 0.003 |
| 10 | 1 | 0.4 |
| 11 | 2.2 | 0.43 |

TEST EXAMPLE 3

In vitro stability test in rat plasma

The testing compound is added to Rat plasma/phosphate buffer (pH=7.4) at 37° C. (the final concentration is 200 μg/ml) and the resulting solution kept at 37° C. Samples are taken at 0, 0.5, 1, 2, 4, and 6 hours. 500 μl of sample is taken in duplicate for each time. To the 500 μl of the sample, 500 μl of ice-cold acetonitrile is added to precipitate the protein, and the product is then vortexed for 30 seconds and centrifuged at 5000 rpm for 10 mins. The supernatant is removed and to it is added 2.0 ml of methylene chloride. The mixture is vortexed for 30 seconds and then centrifuged at 5000 rpm for 10 mins. The upper layer is directly injected onto the HPLC for analysis. The results are shown in the FIGURE.

TEST EXAMPLE 4

In vivo inhibition test for cathepsin B and L

The in vivo inhibition of cathepsin B and L are tested according to the known method (T. Towatari et al, FEBS, 1991, 280, 311–315). Inhibitor is injected intraperitoneally into rodents as a solution in saline containing DMSO or DMSO:PEG400 (1:1) at the doses indicated in Table 2. The rodents are killed after 6 hours, and the liver is perfused with ice-cold saline, and chilled on ice. Sample of 4 g of liver are homogenized in 7 volumes of 0.25 M sucrose. The homogenate is centrifuged at 800 g for 15 min. and the supernatant is centrifuged at 12,000 g for 30 min. The precipitate (crude mitochondrial-lysosomal fraction; ML fraction) is suspended in 2 ml of 0.05 M acetate buffer, pH 5.0, and then freeze-thawed for measurements of cathepsin B and L.

TABLE 2

In vivo inhibition of the inhibitors for cathepsin B and L.

| Compd. | Species | Dosage (mg/kg) | Inhibition[a] Cathepsin B | Cathepsin L |
|---|---|---|---|---|
| Ref. Compd.[b] | rat | 30 | 37% | 30% |
|  | rat | 70 | 56% | 55% |
| Compd. 3 | mouse | 50 | 65% | 55% |

[a]Values are means for 3 animals.
[b]Reference compound is (3S, 4S)-3-{N-(3-phenyl-propionoyl)-L-phenylalanyl}amino-4-(4-(2S-2-amino-2-carboxy ethyl)-phenoxy}-azetidin-2-one.

Although the compounds, the methods of treatment and the methods of making the compounds in accordance with the present invention have been described in connection with preferred embodiments, it will be appreciated by those skilled in the art that modifications not specifically described may be made without departing from the spirit and scope of the invention defined in the following claims.

We claim:

1. A 4-substituted-3-(2-amino-2-cycloalkyl methyl)-acetamido azetidin-2-one compound of formula I, or a pharmaceutically acceptable salt thereof:

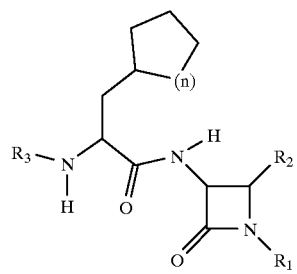

I wherein
n is 1, 2 or 3;
$R_1$ is
hydrogen; or
—$SO_3^- M^+$ wherein M is a hydrogen atom, a metal ion which is selected from sodium, potassium, magnesium, and calcium, or $N^+(R_4)_4$ wherein $R_4$ is a $C_1$–$C_6$ alkyl group;
$R_2$ is
(a) a group —$OCOR_5$ wherein $R_5$ is (i) a $C_1$–$C_6$ alkyl group,
(ii) a $C_2$–$C_6$ alkenyl group,
(iii) a $C_2$–$C_6$ alkynyl group,
(iv) a $C_3$–$C_6$ cycloalkyl group,
(v) a phenyl group,
(vi) a naphthyl group, or
(vii) a monocyclic or bicyclic heterocyclic group, which group (i), (ii), (iii), (iv), (v), (vi), or (vii) is unsubstituted or substituted by 1, 2 or 3 substituents independently selected from
hydroxy,
halogen,
carboxy,
$C_1$–$C_4$ alkyl (which is unsubstituted or substituted at least once with carboxy and/or amino),
$C_1$–$C_2$ alkoxy,
amino,
cyano, and
phenyl and monocyclic or bicyclic heterocyclic groups, which phenyl and heterocyclic groups are unsubstituted or substituted by 1 or 2 substituents independently selected from
hydroxy,
halogen,
carboxy,
$C_1$–$C_4$ alkyl,
$C_1$–$C_2$ alkoxy,
amino, and
cyano;
or (b) a group —$XR_5$ wherein X is selected from the group consisting of O, S, SO, and $SO_2$, and $R_5$ is as defined above;
$R_3$ is hydrogen, —$COOR_5$, —$COR_5$, —$SO_2R_5$, or —$COR_{14}$ wherein $R_5$ is as defined above and $R_{14}$ is amino group which is unsubstituted or substituted at least once with $C_1$–$C_6$ alkyl group which is unsubstituted or substituted at least once with 1 or 2 substitutents selected from hydroxy, halogen, cyano, amino, heterocycle, and phenyl (wherein the heterocycle or phenyl is unsubstituted or substituted at least once by 1 or 2 substituents selected from halogen, hydroxy, cyano, carboxy and amino),
wherein the heterocyclic group as defined in $R_5$ or $R_{14}$ are $C_2$–$C_9$ monocyclic or bicyclic heterocyclic group which have 1–3 heteroatoms selected from nitrogen, sulfur and oxygen.

2. A 4-substituted-3-(2-amino-2-cycloalkyl methyl)-acetamido azetidin-2-one compound of formula I, or a pharmaceutically acceptable salt thereof:

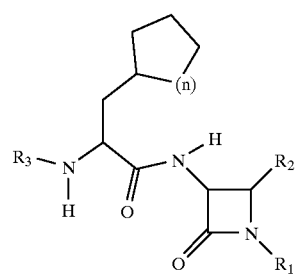

I wherein
n is 1, 2 or 3
$R_1$ is
hydrogen;

—$SO_3^-M^+$ wherein M is a hydrogen atom, a metal ion which is selected from sodium, potassium, magnesium, or calcium, or $N^+(R_4)_4$ wherein $R_4$ is a $C_1$–$C_6$ alkyl group;

$R_2$ is
—$OCOR_5$ wherein $R_5$ is
(i) a $C_1$–$C_6$ alkyl group which is unsubstituted or substituted at least once by 1 or 2 substitutents selected from hydroxy, halogen, and amino; or
(ii) a phenyl group which is unsubstituted or substituted at least once by 1–3 substituents selected from hydroxy, halogen, $C_1$–$C_4$ alkyl group, $C_1$–$C_2$ alkoxy group, and cyano;
—$XR_6$ wherein X is O, S, SO, or $SO_2$; $R_6$ is
(i) a $C_1$–$C_6$ alkyl group which is unsubstituted or substituted at least once by 1 or 2 substitutents selected from hydroxy, halogen, amino or phenyl; or
(ii) a phenyl group which is unsubstituted or substituted at least once by 1–3 substituents selected from hydroxy, halogen, carboxy, and $C_1$–$C_4$ alkyl group which is unsubstituted or substituted at least once with carboxy, amino or both, $C_1$–$C_2$ alkoxy group, cyano or heterocycle group;

$R_3$ is
hydrogen;
—$COOR_7$ wherein $R_7$ is a $C_1$–$C_6$ alkyl group which is unsubstituted or substituted at least once with phenyl and/or heterocycle group;
—$COR_8$ wherein $R_8$ is
(i) a $C_1$–$C_6$ alkyl group which is unsubstituted or substituted at least once by 1 or 2 substitutents selected from hydroxy, halogen, cyano, amino, heterocycle, and phenyl, wherein said heterocycle or phenyl is unsubstituted or substituted at least once by 1 or 2 substituents selected from halogen, hydroxy, cyano, carboxy and amino; or
(ii) an amino group which is unsubstituted or substituted at least once with $C_1$–$C_6$ alkyl group which is unsubstituted or substituted at least once by 1 or 2 substitutents selected from hydroxy, halogen, cyano, amino, heterocycle and phenyl, wherein said heterocycle or phenyl is unsubstituted or substituted at least once by 1 or 2 substituents selected from halogen, hydroxy, cyano, carboxy and amino; or
—$SO_2R_9$ wherein $R_9$ is
(i) a $C_1$–$C_6$ alkyl group which is unsubstituted or substituted at least once with heterocycle and/or phenyl; or
(ii) a $C_2$–$C_4$ alkenyl group which is unsubstituted or substituted at least once with heterocycle and/or phenyl, wherein heterocyclic group as defined in $R_6$, $R_7$, $R_8$ or $R_9$ are $C_2$–$C_9$ mono or bicyclic heterocyclic group which have 1–3 heteroatoms selected from nitrogen, sulfur and oxygen.

3. A compound or salt as recited in claim 2, wherein halogen atoms as substitutents in $R_5$, $R_6$, or $R_9$ are fluorine, chlorine or bromine.

4. A method of regulating a cysteine protease selected from the group consisting of Cathepsin B and Cathepsin L in a patient in need of arthritis treatment, comprising administering to said patient a compound or salt as recited in claim 1 in an amount which is effective for treating arthritis.

5. A compound selected from the group consisting of:
(3S,4S)-3-(2S-2-benzyloxycarbonylamino-2-cyclohexylmethyl-acetamido)-4-acetoxy-azetidin-2-one;
(3S,4S)-3-{2S-2-(3-phenylpropionoyl)amino-2-cyclohexylmethyl-acetamido}-4-acetoxy-azetidin-2-one;
(3S,4S)-3-{2S-2-(3-phenylpropionoyl)amino-2-cyclohexylmethyl-acetamido}-4-{4-(2S-2-amino-2-carboxy-ethyl)-phenoxy}-azetidin-2-one;
(3S,4R)-3-{2S-2-(3-phenylpropionoyl)amino-2-cyclohexylmethyl-acetamido}-4-{4-(2S-2-amino-2-carboxy-ethyl)-phenoxy}-azetidin-2-one;
(3S,4SR)-3-{2S-2-(3-phenylpropionoyl)amino-2-cyclohexylmethyl-acetamido}-4-phenylthio-azetidin-2-one;
(3S,4SR)-3-{2S-2-(3-phenylpropionoyl)amino-2-cyclohexylmethyl-acetamido}-4-phenylsulfonyl-azetidin-2-one;
(3S,4S)-3-{2S-2-(benzylaminocarbonyl)amino-2-cyclohexylmethyl-acetamido}-4-acetoxy-azetidin-2-one;
(3S,4S)-3-{2S-2-(phenylethenylsulfonyl)amino-2-cyclohexylmethyl-acetamido}-4-acetoxy-azetidin-2-one;
(3S,4S)-3-(2S-2-benzyloxycarbonylamino-2-cyclohexylmethyl-acetamido)-4-(3-methyl-phenoxy)-azetidin-2-one;
(3S,4R)-3-(2S-2-benzyloxycarbonylamino-2-cyclohexylmethyl-acetamido)-4-(3-methyl-phenoxy)-azetidin-2-one;
(3S,4S)-3-{2S-2-[3-(pyridin-4-yl)propenoyl]amino-2-cyclohexylmethyl-acetamido}-4-phenoxy-azetidin-2-one; and
(3S,4S)-3-{2S-2-[3-(pyridin-3-yl)propenoyl]amino-2-cyclohexylmethyl-acetamido}-4-phenoxy-azetidin-2-one.

6. A compound or salt as recited in claim 2, wherein $C_1$–$C_4$ alkyl group as substituents in $R_5$, $R_6$, or $R_9$ are branched or straight alkyl chain selected from methyl, ethyl, propyl, 2-methyl propyl, butyl and 1,1-dimethyl ethyl.

7. A compound or salt as recited in claim 2, wherein said compound is the L isomer of the asymmetric carbon having the cycloalkyl methyl and amino substituents thereon.

8. A compound or salt as recited in claim 2, wherein said compound is selected from the 3S, 4S and 3S, 4R diastereoisomers and the 3S, 4SR racemate of the C3 and C4 asymmetric carbon of the azetidinone nucleus.

9. A pharmaceutical composition comprising a compound or salt as recited in claim 1 and a pharmaceutically acceptable carrier.

10. A salt as recited in claim 2, wherein said salt comprises a component selected from sodium, potassium, magnesium, calcium, hydrogen chloride, tartaric acid, succinic acid, fumaric acid and p-toluenesulfonic acid.

11. A compound or salt as recited in claim 8, wherein said compound is selected from the isomers in which C3 and C4 are cis to each other.

12. A compound or salt as recited in claim 11, wherein $C_1$–$C_6$ alkyl group as substituents in $R_4$, $R_5$, $R_6$, $R_8$, or $R_9$ are selected from methyl, ethyl, propyl, 1-methylethyl, butyl, 1-methylpropyl, 2-methylprop-1-yl, 2-methylprop-2-yl, pentyl, 3-methylbutyl, and hexyl.

13. A compound or salt as recited in claim 4, wherein $C_2$–$C_4$ alkenyl group as defined in $R_9$ are selected from ethenyl, 1-propenyl, 2-propenyl, 1-butenyl, and 3-butenyl.

14. A compound or salt as recited in claim 5, wherein heterocyclic group as defined in $R_6$ $R_7$, $R_8$ or $R_9$ are selected from thiophene, pyridine, 1,2,3-triazole, 1,2,4-triazole, quinoline, benzofuran, benzothiophene, morpholine, thiomorpholine, piperizine, and piperidine.

* * * * *

UNITED STATES PATENT AND TRADEMARK OFFICE
CERTIFICATE OF CORRECTION

PATENT NO. : 5,916,887

DATED : June 29, 1999

INVENTOR(S) : SINGH et al.

It is certified that error appears in the above-identified patent and that said Letters Patent is hereby corrected as shown below:

Column 5, line 11, delete "cystein", insert therefor

-- cysteine --

Column 11, line 44, delete "$CDCl_3-d_6$", insert therefor

-- $CDCl_3$ --

Column 12, line 3, delete "$CDCl_3-d_6$", insert therefor

-- $CDCl_3$ --

Signed and Sealed this

First Day of February, 2000

Attest:

Q. TODD DICKINSON

*Attesting Officer*  *Acting Commissioner of Patents and Trademarks*